United States Patent [19]

Barrett et al.

[11] Patent Number: 4,933,505

[45] Date of Patent: Jun. 12, 1990

[54] METHOD OF PREPARING STEREOSPECIFIC NITROALDOLS

[75] Inventors: Anthony G. M. Barrett; Christopher D. Spilling, both of Evanston, Ill.

[73] Assignee: Northwestern University, Evanston, Ill.

[21] Appl. No.: 229,009

[22] Filed: Aug. 5, 1988

[51] Int. Cl.$^5$ ............................................. C07C 79/22
[52] U.S. Cl. .................................... 568/705; 568/704
[58] Field of Search ................................ 568/704, 705

[56] References Cited

U.S. PATENT DOCUMENTS

| | | | |
|---|---|---|---|
| 2,132,353 | 10/1938 | Hass | 568/704 |
| 2,475,996 | 7/1946 | Smith | 568/705 |
| 2,543,957 | 3/1951 | Crooks et al. | 568/705 |
| 3,005,854 | 10/1961 | Braun et al. | 568/705 |
| 3,660,500 | 5/1972 | Hardtman et al. | 568/705 |

FOREIGN PATENT DOCUMENTS

| | | | |
|---|---|---|---|
| 820260 | 9/1959 | United Kingdom | 568/705 |
| 1201209 | 8/1970 | United Kingdom | 568/705 |

OTHER PUBLICATIONS

Seebach, et al., *Helv. Chim. Acta*, 65:1101 (1982).
Seebach, et al., *J. Am. Chem. Soc.*, 107:3601 (1985).
Hanessian et al., *Tetrahedon Lett.*, 16:1261 (1985).
Bordwell and Arnold, "The Stereochemistry of the Hydrogenation of cis-and trans-1-Nitro-2-phenylcyclohexane Using W-2 Raney Nickel Catalyst", vol. 27, 4426–4428, Dec., 1962.
Bordwell and Garbish, Jr., "Nitrations with Acetyl Nitrate. IV.", vol. 28, 1765–1769, July, 1963.
Sundberg and Bukowick, *J. Org. Chem.*, 33:4098–4102 (1968).
Bordwell and Birankowski, "Nitrations with Acetyl Nitrate. V.", vol. 32, 629–634 (1967).
Barrett, Grabowski, Russell, *J. Org. Chem.*, 51:1012–1015 (1986).
Nielsen, "The Isomeric Dinitrocyclohexanes. II. Stereochemistry", vol. 27, 1998–2001 (1962).
Reetz and Peter, *Tetrahedon Lett.*, 22:4691–4694 (1981).

*Primary Examiner*—Warren B. Lone
*Attorney, Agent, or Firm*—Tilton, Fallon, Lungmus & Chestnut

[57] ABSTRACT

A method of controlling the diastereoselectivity of the nitroaldol reaction by the use of titanium, zirconium and aluminum based Lewis acids is disclosed. In a preferred embodiment, the reaction of lithium nitronate anion with aldehydes in THF/CH$_2$Cl$_2$ at reduced temperature in the presence of isopropoxy titanium trichloride (TiCl$_3$(OPr$^i$)) yields nitro alcohols enriched in the erythro diastereomer. Erythro-threo ratios of 11.2:1–3.4:1 for aromatic aldehydes and 3.8:1–1:1 for aliphatic aldehydes are typically obtained.

15 Claims, No Drawings

METHOD OF PREPARING STEREOSPECIFIC NITROALDOLS

BACKGROUND OF THE INVENTION

The nitroaldol or Henry reaction is one of the classical C, C- bond forming processes. Referring to Scheme I, the nitroaldol reaction furnishes the 1, 2 -functionalized nitro alcohols A, precursors of the symmetrical ($R^1=R^2$) and nonsymmetrical ($R^1 \neq R^2$) aminoalcohols B.

Nitro alcohols are frequently used as intermediates in synthesis of $\beta$-amino alcohol derivatives. For example, they are useful in the synthesis of Chloramphenicol, J. Controulis et al. *J. Am. Chem. Soc.*, 1949, 71, 2463 and of ephedrine 7a, F. Hoover et al J. Org. Chem. 1967, 12, 506 and norephedrine 7b.

The nitroaldol reaction has been extensively studied, G. Verlag in *Methoden der Organischen Chemie* 1971 (Houben-Weyl). Vol. XII and R. G. Coombes in Comprehensive Organic Chemistry 1979 (Eds., D. Barton & W. Olles) p. 303 Pergamon, Oxford. However, in the conventional process for preparing nitro alcohols, identified as the nitroaldol or Henry reaction, there is no control of stereoselectivity, except in cyclic systems, and this problem has hardly been addressed. The lack of selectivity is due to the reversibility of the reaction and the facile epimerization at the nitro-substituted C-atom. The nitro alcohols of this type ($R^1R^2=$) occur in two diastereomeric forms, the erythro - (C) and the threo - (D) isomers,. A stereoselective synthesis of either of these isomers is desirable.

Seebach has reported that doubly deprotonated nitro alkanes 1 in Scheme II react with aldehydes to yield intermediate nitronate alkoxides 2, Seebach et al *Helv Chim. Acta* 1982 65, 1101 and Seebach et al J. Am. Chem. Soc. 1985 107 3601 It appears that kinetic reprotonation at $-100°$ C. in polar solvents yield nitro alcohols enriched in the threo diastereoisomer 3 in a ratio of erythro-threo of 47:3–18:7. Conversely, Seebach also reports the reprotonation of the t-butyldimethylsilyloxy to give nitro alkanes 4 enriched in the erythro diastereoisomer 41:9–19:1. Seebach observed high erythro selectivity 19:1–4:1 with a fluoride catalyzed reaction of silyl nitronates 5 with aldehydes under appropriate reaction conditions, such as very low temperature (below $-80°$ C.) and the use of stabilizing agents and protecting groups.

Hanessian et al., *Tetrahedron Lett* 1985, 16, 1261 has observed variation in selectivity in the reaction of (S)-benzyloxypropionaldehyde with methyl 3 - nitropropionate using zinc or magnesium salts and potassium t-butoxide in THF.

There is a need for a process to control the diastereoselectivity of the nitroaldol reaction without the disadvantages seen in the prior art: starting the reaction with two equivalents of base, using a highly reactive anion, using a sensitive protective group or requiring exact experimental control over the process.

SUMMARY OF THE INVENTION

The present invention relates to a relatively simple method of controlling the diastereoselectivity of the nitroaldol reaction comprising deprotonating a nitroalkane to produce a monoanion under conditions of reduced temperature and inert atmosphere, such as nitrogen, admixing a titanium, zirconium or aluminum complex to the monoanion to form a titanium, zirconium or aluminum nitronate complex, admixing an aldehyde which reacts with the nitronate complex forming a nitro alcohol (threo) warming to room temperature and separating the nitro alcohols enriched in the erythro diastereomer.

More particularly, a preferred method comprises reacting alkyl nitronate, formed by the action of n-butyllithium on nitroalkanes in tetrahydrofuran solution with aldehydes in the presence of isopropoxytitanium trichloride to yield nitro alcohols that are predominantly erythro, having erythro-threo ratios of about 11:1–3 1 when aromatic aldehydes are utilized and about 4:1–1:1 when aliphatic aldehydes are utilized.

DETAILED DESCRIPTION OF THE INVENTION

A relatively simple method has been devised to control the diastereoselectivity of the nitroaldol or Henry reaction to provide a major proportion of erythro $\beta$-nitro alcohols on a consistent basis. The new method does not require the use of protecting groups, highly reactive anions, exacting control over the process parameters nor large quantities of the base material.

It has now been found that in order to produce $\beta$-nitro alcohols, a titanium, zirconium or aluminum based Lewis acid may be utilized to selectively produce the desired stereoisomer. A preferred catalyst is a titanium complex. Preferably, isopropoxytitanium trichloride is the titanium complex utilized in this procedure. It is formed by admixing 1 M solution of titanium tetrachloride and dichloromethane. The mixture is cooled to $-78°$ C. and titanium isopropoxide is added to form the titanium complex isopropoxytitanium trichloride, which precipitates as a solid which is redissolved in tetrahydrofuran. In another embodiment, n-propoxy zirconium trichloride may be utilized to produce erythro - $\beta$-nitro alcohols, however, the yields are not as high as when the titanium complex is utilized. The zirconium complex is formed by admixing zirconium isopropoxide at room temperature to a suspension of zirconium chloride in dichloromethane. After the suspension has dissolved, benzaldehyde is added which causes the zirconium trichloride to precipitate as a solid which is redissolved in tetrahydrofuran.

In one further embodiment, ethyl aluminum dichloride may be utilized as a catalyst in the present invention.

Typically, stoichiometric amounts of catalysts are utilized in the process of the present invention in the following ratio: 1 part catalyst : 1 part aldehyde : 2 parts nitro compound.

In one embodiment of the present invention, erythro $\beta$-nitro alcohol are produced as follows:

Under an inert atmosphere, n-butyllithium (1.6M in hexane, 6.24 mL) is added dropwise with stirring to a solution of the nitroalkane (10 mmol) in tetrahydrofuran (THF) (12mL) at a reduced temperature, preferably $-78°$ C. Other solvents may be utilized which dissolve the nitroalkane. By reduced temperature, it is meant a temperature which is effective to allow the reaction to be completed, and in this instance, to produce the nitronate anion. After about 15 minutes a solution of isopropoxytitanium trichloride (TiCl$_3$(OPr$^i$) (5 mmol) in THF (2 mL) and CH$_2$Cl$_2$ (3mL) solution is added. After a further 15 minutes the aldehyde (5 mmol) is added and the mixture allowed to warm up to room temperature which takes about 30 minutes. Stirring is continued for a further 3.5 hours at room temperature and the mixture is quenched with an aqueous slurry of disodium EDTA (1.86g, 5mmol), and extracted with Et$_2$O (3×7 mL). The combined Et$_2$O fractions are then washed with dilute acid, preferably hydrochloric acid (2 M, 75 mL), aqueous sodium bicarbonate (75 mL) and water (75 mL), dried and evaporated in vacuo. Flash chromatography using hexane-Et$_2$O yields the nitro alcohol products.

The step of warming the mixture to room temperature causes protonation-reprotonation of the nitro alcohol to produce a predominance of the erythro isomer. If the nitro alcohols would be extracted without the warming process, a predominance of threo isomer would be produced.

The foregoing process can be carried out with both aliphatic and aromatic aldehydes. When aromatic aldehydes are utilized in the process, yields of erythro over the threo isomer are generally higher. Overall the erythro-threo ratio may range from about 11.2:1 to 1.1:1.

In accordance with the present invention, "nitro alkanes" are defined as primary nitro alkanes wherein the nitro group is attached to the last carbon in the aliphatic carbon chain. With the nitro group attached to the last carbon in the single aliphatic carbon chain are two hydrogen atoms. The length of the aliphatic carbon chain is immaterial. More specifically the nitro alkane may be represented by the following formula:

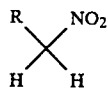

Primary nitro alkane where R represents an unsubstituted or substituted alkyl, cycloalkyl or aryl group with substitution being inert to the reaction conditions e.g. ether, aryl, hydroxyl, carboxylic acid and ester groups. The length of the carbon chain is immaterial. However, preferably it may be about 1–30 carbon atoms. The size of the cyclic structures is immaterial.

The term "aldehyde" refers to both aliphatic and aromatic aldehydes. The aliphatic aldehyde is generally unsubstituted at the α carbon, however, the reaction does occur with a carbonyl group attached at the β carbon position. Aromatic aldehydes can be either unsubstituted or substituted at the ortho, meta or para positions. Suitable substitution groups include nitro, alkyl ether, alkyl, halogen, halogen alkyl, carboxylic acid esters and the like. All substitution groups may be groups which are inert to reduction or hydrogenation.

Without being limiting, nitro alcohols are therefore defined by the nature of the reaction and the corresponding aldehyde from which they are produced.

Table I shows the results of the foregoing process of the present invention when an aromatic aldehyde, p-Nitrobenzaldehyde, is utilized and Table II shows the results of the process of the present invention when various aromatic and aliphatic aldehydes are utilized.

TABLE I

| Reaction of Alkyl Nitronates with p-Nitrobenzaldehyde | | |
|---|---|---|
| Nitroalkane | Yield (% isolated) | Erythro:Threo ratio[a,b] |
| a. CH$_3$(CH$_2$)$_4$CH$_2$NO$_2$ | 81 | 3.9:1 |
| b. EtO$_2$C(CH$_2$)$_2$CH$_2$NO$_2$ | 72 | 7:1 |
| c. THPOCH$_2$CH$_2$NO$_2$ | 83 | 4:1 |

TABLE I-continued

| Reaction of Alkyl Nitronates with p-Nitrobenzaldehyde | | |
|---|---|---|
| Nitroalkane | Yield (% isolated) | Erythro:Threo ratio[a,b] |
| d. CH$_3$CH$_2$CH$_2$NO$_2$ | 72 | 7:1 |

[a] determined by the $^1$H NMR spectrum of the crude product[1]
[b] all new compounds were fully authenticated by spectroscopic data and microanalyses or high resolution mass spectra

TABLE II

| Reaction of the Nitropropane Anion with Aldehydes | | | |
|---|---|---|---|
| Aldehyde | No. of equiv. of nitronate | Yield (% isolated) | Erythro:Threo ratio[a,b] |
| a. p-O$_2$NC$_6$H$_4$CHO | 1 | 50 | 5.6:1[c] |
| b. PhCHO | 1 | 41 | 4.6:1 |
|  | 2 | 61 | 6:1 |
| c. p-MeOC$_6$H$_4$CHO | 1 | 21 | 1.7:1 |
|  | 2 | 47 | 3.4:1 |
| d. p-O$_2$NC$_6$H$_4$CHO | 1 | 46 | 9.4:1[c] |
|  | 2 | 65 | 6:1[c] |
| e. p-F$_3$CC$_6$H$_4$CHO | 1 | 38 | 7.3:1 |
|  | 2 | 57 | 6.7:1 |
| f. p-MeO$_2$CC$_6$H$_4$CHO | 1 | 45 | 11.2:1[c] |
|  | 2 | 71 | 5.7:1[c] |
| g. β-naphthaldehyde | 2 | 61 | 4.9:1 |
| h. (E)-Cinnamaldehyde | 2 | 43 | 8:1[d] |
| i. CH$_3$(CH$_2$)$_5$CHO | 1 | 13 | 3.8:1[d] |
|  | 2 | 28 | 3.8:1[e] |
| j. CH$_3$(CH$_2$)$_3$CHO | 2 | 27 | 2.9:1[e] |
| k. t-BuCHO | 2 | 0 | — |
| l. EtO$_2$CCHO | 2 | 36 | 1:1[e] |

[a] determined by the $^1$H NMR spectrum of crude product[1];
[b] all new compounds were fully authenticated by spectroscopic data and microanalyses or high resolution mass spectra
[c] recrystallization gave a single diastereoisomer;
[d] chromatography gave a single diastereoisomer. The ratio was determined by the $^{13}$C NMR spectrum of the crude product[1];
[e] determined by the $^{13}$C NMR spectrum of the isolated β-nitro alcohol fraction.

In order to illustrate the method of obtaining erythro β-nitro alcohols, reference is made to the following examples which are, however, not to be interpreted as limiting the scope of this invention in any respect.

EXAMPLE 1

Erythro-1(4-nitrophenyl)-2-nitro-butan-1-ol n-BuLi (1.6 M in hexane, 6.24 mL) was added dropwise with stirring to a solution of nitropropane (0.9mL, 10mmol) in THF (12 mL) at −78° C. After 15 minutes a solution of TiCl$_3$(OPr$^{iso}$) (5 mmol) in THF (2 mL) and CH$_2$Cl$_2$ (3 mL) solution was added. After a further 15 minutes 4-nitrobenzaldehyde (0.75 mL, 5 mmol) in CH$_2$Cl$_2$ (4 mL) was added and the mixture allowed to warm up to room temperature (~30 min). Stirring was continued for a further 3.5 hours at room temperature and the mixture was quenched with an aqueous slurry of disodium EDTA (1.86 g, 5mmol) and extracted with Et$_2$O (3×75 mL). The combined Et$_2$O fractions were washed with dilute hydrochloric acid (2 M, 75 mL), aqueous sodium bicarbonate (75 mL) and water (75 mL), dried and evaporated in vacuo. Flash column chromatrography [Si$_2$, hexane:Et$_2$O, 3:1 v/v] gave 1-(4-nitrophenyl)-2-nitro-butan-1-ol (0.86 g, 72%) Erythro:threo ratio 7:1.

EXAMPLE 2

Threo-1-Phenyl-2-Nitro-butan-1-ol n-BuLi (1.6 M in hexane, 3.12 mL), was added dropwise with stirring to a solution of nitropropane (0.45 mL, 5 mmol) in THF (8 mL) at −78° C. After 15 minutes the complex formed by the addition of benzaldehyde (0.5 mL, 5 mmol) and THF (2 mL) to TiCl$_3$(OPr$^{iso}$) (5 mmol) in CH$_2$Cl$_2$ (3.75 mL) was added. Stirring was continued for 1h then the mixture was quenched with an aqueous slurry of disodium EDTA (1.86 g, 5 mmol) and extracted with Et$_2$O (3×74 mL). The combined Et$_2$O fractions were washed with dilute hydrochloric acid (2 M, 75 mL), aqueous sodium bicarbonate (75 mL) and water (75 mL), dried and evaporated in vacuo. Flash column chromatography [SiO$_2$, hexane, Et$_2$O, 8:1 v/v] gave 1-phenyl-2-nitro-butan-1-ol (0.024 g, 2.5%). Erythro:threo ratio 1:9.4.

EXAMPLE 3

Threo-2-(3-phenyl-2-nitro-3-hydroxy-propanoxy) tetrahydro-pyran n-BuLi (1.6 M in hexane, 3.12 mL) was added dropwise with stirring to a solution of 2(2-nitroethoxy) tetrahydropyran (0.87 g, 5 mmol) in THF (8 mL) at −78° C. After 15 minutes, the complex formed by the addition of benzaldehyde (0.5 mL, 5 mmol) and THF (2 mL) to TiCl$_3$(OPr$^{iso}$) (5 mmol) in CH$_2$Cl$_2$ (3.75 mL) was added. Stirring wa continued for 1h then the mixture was quenched with an aqueous slurry of disodium EDTA (1.86 g, 5 mmol) and extracted with Et$_2$O (3×75 mL). The combined Et$_2$O fractions were washed with dilute hydrochloric acid (2 M, 75 mL), aqueous sodium bicarbonate (75 mL) and water (75 mL), dried and evaporated in vacuo. Flash column chromatography [SiO$_2$, hexane, Et$_2$O, 4:1 v/v] gave the 2-(3-phenyl-2-nitro3-hydroxy-propanoxy) tetrahydro-pyran (0.073 g, 5%). Erythro:threo ratio 1:6.5

EXAMPLE 4

Erythro-1-Naphthyl-2-nitro-butan-1-ol n-BuLi (1.6 M in hexane, 6.24 mL) was added dropwise with stirring to a solution of nitropropane (0.9 mL, 10 mmol) in THF (12 mL) at −78° C. After 15 minutes a solution of TiCl$_3$(OPr$^{iso}$) (5 mmol) in THF (2 mL) and CH$_2$Cl$_2$ (3 mL) solution was added. After a further 15 minutes α-naphthaldehyde (0.78 mL, 5 mmol) in CH$_2$Cl$_2$ (1 mL) was added and the mixture allowed to warm up to room temperature (~30 min.). Stirring was continued for a further 3.5 hours at room temperature and the mixture was quenched with an aqueous slurry of disodium EDTA (1.86 g, 5 mmol) and extracted with Et$_2$O (3×74 mL), aqueous sodium bicarbonate (75 mL) and water (75 mL), dried and evaporated in vacuo. Flash column chromatography [SiO$_2$, hexane:ET$_2$O, 4:1 v/v] gave 1-naphthyl-2-nitro-butan-1-ol (0.75 g, 61%) Erythro:threo ratio 4.9:1.

EXAMPLE 5

Erytho-1-Phenyl-2-Nitro-butan-1-ol n-BuLi (1.6 M in hexane, 6.24 mL) was added dropwise with stirring to a solution of nitropropane (0.9 mL, 10 mmol) in THF (12 mL) at −78° C. After 15 minutes a solution of TiCl$_3$(OPr$^{iso}$) (5 mmol) in THF (2 mL) and CH$_2$Cl$_2$ (3 mL) solution was added. After a further 15 minutes benzaldehyde (0.5 mL, 5 mmol) was added and the mixture allowed to warm up to room temperature (~30 min.). Stirring was continued for a further 3.5 hours at room temperature and the mixture was quenched with an aqueous slurry of disodium EDTA (1.86 g, 5 mmol) and extracted with Et$_2$O (3×75 mL). The combined Et$_2$O fractions were washed with dilute hydrochloric acid (2 M, 75 mL), aqueous sodium bicarbonate (75 mL) and water (75 mL), dried and evaporated in vacuo. Flash column chromatography (SiO$_2$, hexane:Et$_2$O, 6:1 v.v] gave 1-phenyl-2-nitro-butan-1-ol (0.57 g, 61%) erythro:threo ratio 6:1.

EXAMPLE 6

Erythro-1-(4-nitrophenyl)-2-nitro-heptan-1-ol n-BuLi (1.6 M in hexane, 6.24 mL) was added dropwise with stirring to a solution of nitrohexane (1.4 mL, 10 mmol) in THF (12 mL) at −78° C. After 15 minutes a solution of TiCl$_3$(OPr$^{iso}$) (5 mmol) in THF (2 mL) and CH$_2$Cl$_2$ (3 mL) solution was added. After a further 15 minutes 4-nitrobenzaldehyde (0.75 mL, 5 mmol) in CH$_2$Cl$_2$ (3 mL) was added and the mixture allowed to warm up to room temperature ([18] 30 min.). Stirring was continued for a further 3.5 hours at room temperature and the mixture was quenched with an aqueous slurry of disodium EDTA (1.86 g, 5 mmol) and extracted with Et$_2$O (3×75 mL), aqueous sodium bicarbonate (75 mL) and water (75 mL), dried and evaporated in vacuo. Flash column chromatography [SiO$_2$, hexane:Et$_2$O, 4:1 v/v] gave 1-(4-nitrophenyl)2 -nitro-heptan-1-ol (1.13 g, 81% Erythro:threo ratio 3.9:1

EXAMPLE 7 n-Propoxy Zirconium Trichloride Mediated Henry Reaction (a) Complex Formation:

Zirconium isoproxide (0.38 mL) was added at room temperature to a suspension of zirconium chloride (0.874 g) in dichloromethane (2 mL). After the suspension had dissolved Benzaldehyde (0.53 g, 5 mmole) and THF (1 mL) were added.

(b) n-BuLi (1.6 M hexane sol$^n$, 3.12 mL) was added dropwise with stirring to a solution of nitropropane (0.45 mL, 5 mmol) in THF (4 mL at −78° C. After 20 minutes the complex (as prepared above) was added and the solution allowed to warm to room temperature. After a further 4 hours the reaction was quenched at 0° C. with an aqueous slurry of disodium EDTA (1.86 g in 10 mL water). The mixture was diluted with water (50 mL) and extracted with Et$_2$O (3×50 mL). The combined Et$_2$O extracts were washed with hydrochloric acid (2 M, 50 mL), aqueous sodium bicarbonate (saturated, 50 mL) and water (50 mL, dried and evaporated in vacuo. Flash column chromatography [SiO$_2$ hexane, Et$_2$O 6:1] gave 1-phenyl-2-nitro-1-propanol (0.271 g, 28%) Erythro:threo ratio 4.6:1.

EXAMPLE 8

Ethyl Aluminum Dichloride Mediated Henry Reaction

To a solution of nitropropane (0.45 g, 0.005 moles) in dichloromethane (25 mL) at 0° C. was added triethylamine (0.67 mL, 0.005 moles) followed by ethyl aluminum dichloride (1.0 M in hexane, 5 mL, 0.005 moles). After 15 minutes benzaldehyde (0.5 mL 0.005 moles) was added and the solution allowed to warm to room temperature. After a further 3 hours the reaction was cooled in ice to a temperature of 5° C. and quenched with pH 7.0 phosphate buffer. The organic layer was separated, dried and evaporated in vacuo. Flash column chromatography [SiO$_2$, 6:1 hexane, Et$_2$O] gave 1-phenyl-2-nitro-1-butanol (0.28 g, 29%) Erythro:threo ratio 1:1.6.

A similar reaction quenched after 50 minutes gave an Erythro:threo of 2.8:1.

What is claimed is:

1. Method of preparing stereospecific nitro alcohols comprising:

deprotonating a nitroalkane in a deprotonating solution at a reduced temperature and under an inert gas, said conditions being effective to form a nitronate anion;

admixing the anion with a Lewis acid metal complex at a reduced temperature effective to form a nitronate, the metal of said complex being selected from the group consisting of titanium, zirconium, and aluminum;

slowly warming the mixture to a temperature effective for forming an erythro nitroaldo; and separating the erythro nitroaldol from the reaction mixture.

2. The method of claim 1 wherein the catalyst is isopropoxytitanium chloride.

3. The method of claim 1 wherein the catalyst is n-propoxy zirconium trichloride.

4. The method of claim 1 wherein the catalyst is ethyl aluminum dichloride.

5. The method of claim 1 wherein isopropoxytitanium chloride formed by admixing 1 molar solutions of titanium tetra-chloride in dichloromethane with titanium isopropoxide until the titanium complex precipitates as a solid.

6. The method of claim 1 wherein the aldehyde may be aromatic or aliphatic.

7. The method of claim 1 wherein the reduced temperature is $-78°$ C.

8. The method of claim 1 wherein the inert gas is nitrogen.

9. The method of claim 1 wherein the yield of erythro to threo is in the range of about 11:1 to about 1:1.

10. The method of claim 1 wherein the nitro alcohols are separated from the aldehyde nitronate reaction mixture without warming said mixture to room temperature to produce the threo nitroalcohol.

11. The method of claim 1 wherein 1 part catalyst, 1 part aldehyde and 2 parts nitroalkane are utilized to produce the nitroaldol.

12. Method of preparing stereospecific nitro alcohols comprising: reacting a primary nitro alkane anion with a Lewis acid metal complex to form a nitronate, said metal being selected from the group consisting of titanium, zirconium, and aluminum, said reaction being carried out at a reduced temperature effective for producing the nitronate; admixing the nitronate-containing reaction mixture with an aldehyde; slowly warming the resulting mixture to a temperature effective for forming an erythro nitroaldol; and recovering the erythro nitroaldol from the reaction mixture.

13. The method of claim 1 in which said nitro alkane anion is nitropropane.

14. The method of claim 12 in which said aldehyde is p-nitrobenzaldehyde.

15. The method of claim 14 in which said nitro alkane is nitropropane.

* * * * *